(12) United States Patent
Miyazaki (10) Patent No.: US 6,352,520 B1
(45) Date of Patent: Mar. 5, 2002

(54) HEMOSTATIC VALVE FOR A CATHETER INTRODUCER

(75) Inventor: Masamitsu Miyazaki, Nagoya (JP)

(73) Assignee: Goodman Co., LTD (JP)

( * ) Notice: Subject to any disclaimer, the term of this patent is extended or adjusted under 35 U.S.C. 154(b) by 0 days.

(21) Appl. No.: 09/235,110

(22) Filed: Jan. 21, 1999

(30) Foreign Application Priority Data

Apr. 24, 1998 (JP) ............................................. 10-114745

(51) Int. Cl.⁷ .......................... A61M 5/178; A61M 5/00
(52) U.S. Cl. ................... 604/167.03; 604/256
(58) Field of Search ................................ 604/256, 158, 604/164, 169, 167, 246, 167.01, 167.02, 167.03, 167.04, 539; 411/542, 313–314

(56) References Cited

U.S. PATENT DOCUMENTS

| | | | |
|---|---|---|---|
| 4,909,798 A | | 3/1990 | Fleschhacker et al. ...... 604/256 |
| 4,960,412 A | * | 10/1990 | Fink ............................ 604/167 |
| 5,000,745 A | * | 3/1991 | Guest et al. ................ 604/167 |
| 5,092,857 A | * | 3/1992 | Fleischhacker .............. 604/256 |
| 5,167,637 A | * | 12/1992 | Okada et al. ................ 604/167 |
| 5,226,879 A | * | 7/1993 | Ensminger et al. ........... 604/93 |
| 5,350,363 A | * | 9/1994 | Goode et al. ................ 604/167 |
| 5,858,007 A | * | 1/1999 | Fagan et al. ................. 604/256 |
| 6,083,203 A | * | 7/2000 | Yoon ............................ 604/167 |

FOREIGN PATENT DOCUMENTS

JP     2949     1/1990

\* cited by examiner

*Primary Examiner*—Sharon Kennedy
(74) *Attorney, Agent, or Firm*—Pearson & Pearson, LLP (57) ABSTRACT

Along with a reduction in the resistance of a catheter in passing through a valve in an catheter introducer, the hemostatic effect is improved. A main body of the valve is made of a 3-layer structure, and both front and back layers are provided with narrow slits B, B having a crossing at the center, and the interlayer is provided with narrow slit B having a cut closed by contact with the tip of flap 8 protruded from both sides, where the narrow slit in the interlayer is provided as a penetration hole having a round section with the outer periphery in contact with both the sides of the interlayer and in a perpendicular direction to the narrow slits B, B in the back and front layers, as shown in FIG. 8.

10 Claims, 9 Drawing Sheets

HEMOSTATIC VALVE FOR A CATHETER INTRODUCER

FIELD OF THE INVENTION

The present invention relates to a hemostatic valve in a catheter introducer which is utilized for introducing e.g. an angiographic catheter into a sheath previously penetrated into a blood vessel in order to introduce the catheter into the blood vessel through the sheath.

BACKGROUND ART

The catheter introducer is provided with a hemostatic valve which enables removal and insertion of a catheter, and when the catheter is removed, this hemostatic valve should be closed to exhibit the hemostatic function.

Accordingly, a structure in which an open cut made in one side and another open cut in the other side are allowed to intersect partially or are connected to each other via a penetration hole is known as described in Japanese Patent Publication No. 949/1990.

A wide variety of patterns in the form of one letter, X shape, Y shape etc. are proposed for the cut described above, and any cut i.e. slit is closed like those made with a knife.

Because a slit such as that cut with a knife is strongly closed, the resistance of a catheter upon insertion into the slit is so great that the insertion involves pulling its surrounding portion into the slit, thus causing the operability of the catheter to worsen and resulting in great deformation of the outer periphery.

If the cut is formed as a narrow slit and pushed into a valve accommodating portion (valve room) to be given tightening force from the surrounding so as to permit the slit to be closed, not only operability is improved but the hemostatic function can also be satisfied.

In this case, however, too high a tightening force would cause an increase in the resistance of a catheter in passing through the slit to thereby decreasing it operability, whereas low tightening force would cause blood leakage. Even if the tightening force is suitable, the operability and hemostatic function would be affected adversely if the elasticity of the valve is changed due to a difference in frequency of use.

SUMMARY OF THE INVENTION

The present invention relates to a hemostatic valve for a catheter introducer for decreasing passage resistance by conferring the hemostatic function on the valve solely and minimizing tightening force, wherein a main body of the valve composed of plural layers is provided with at least one of a small penetration hole penetrating the center of each layer, a narrow slit having a crossing at the center and a cut having crossing at the center such that the small penetration hole or the narrow slit is allowed to be present in at least one layer, and a closed flap is provided at an opening in the boundary between the layer provided with the small penetration hole or the narrow slit and a layer adjacent to said layer.

A section of the small penetration hole is made circular, and the opening of said penetration hole is made to have a spherical face in contact with the boundary of a layer, or a section of the small penetration hole is made polygonal and the opening of said penetration hole is made to have a polygonal pyramid-shaped face having a tip in contact with the boundary of a layer, or a section of the opening of the narrow slit is made a curved face having a tip in contact with the boundary of a layer, or a section of the opening of the narrow slit is formed into a polygonal shape having a tip in contact with the boundary of a layer, whereby said flap can be formed.

The main body of the valve is provided on the face at the side for inserting a catheter, with a groove along the outer periphery.

DETAILED DESCRIPTION OF THE INVENTION

The hemostatic valve of the present invention is described by reference to the drawings.

Figure 1:
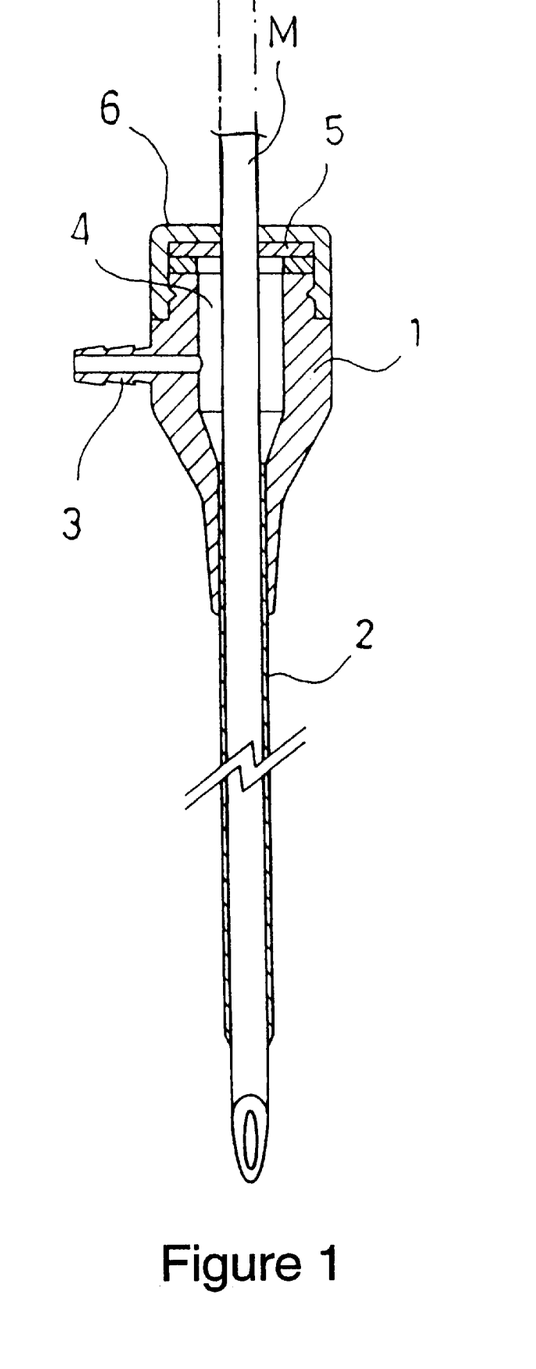
FIG. 1 is a drawing showing the structure of a catheter introducer.

FIG. 1 shows the whole of the catheter introducer, wherein the main body 1 includes sheath 2 integrated into one body at the top and the branched tube 3 projected at the side.

The main body 1 is released at the back and provided therein with a valve accommodating portion 4 leading to the penetration hole of the sheath 2, and the hemostatic valve 5 is set in the inside of the valve accommodating portion 4.

Further, the opening at the back of the valve accommodating portion 4 can be closed with a cap body 6, and catheter M can be inserted into the central hole of the cap body 6, and by penetrating it through the hemostatic valve 5, its top can appear from the top of the sheath 2.

Figure 2:
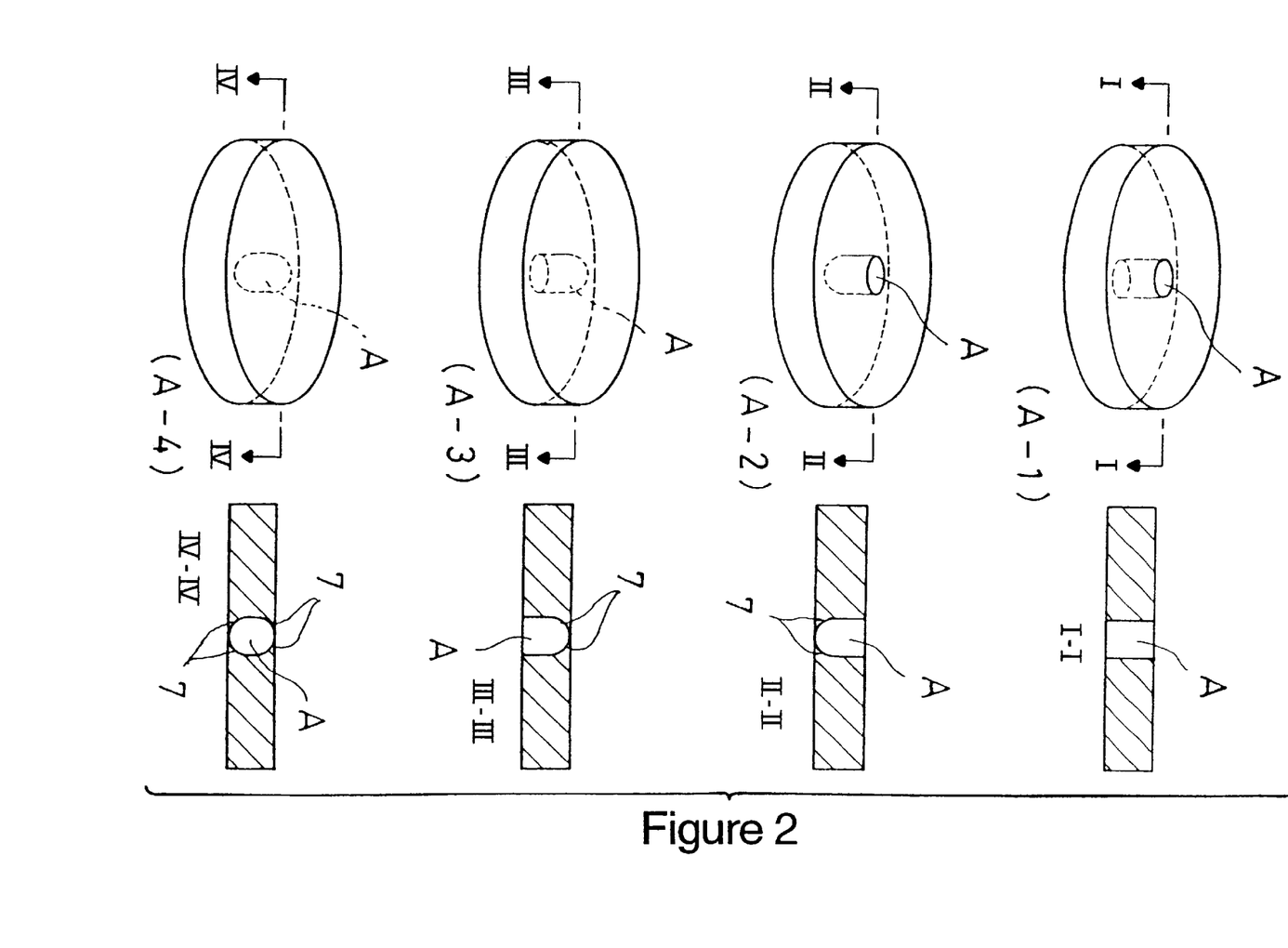
FIG. 2 is a drawing showing a pattern of small penetration holes.
Figure 3:
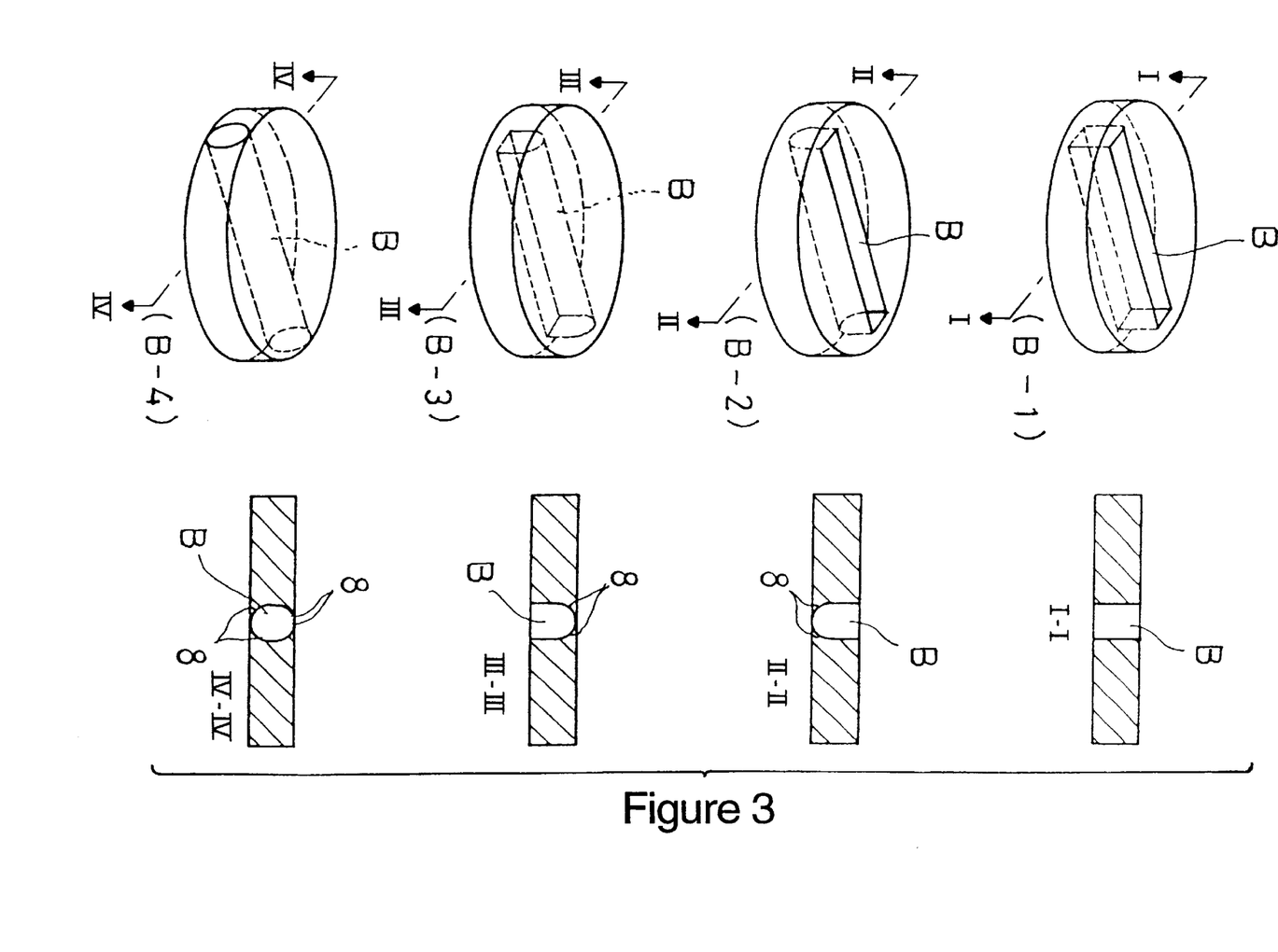
FIG. 3 is a drawing showing a pattern of narrow slits.
Figure 5:
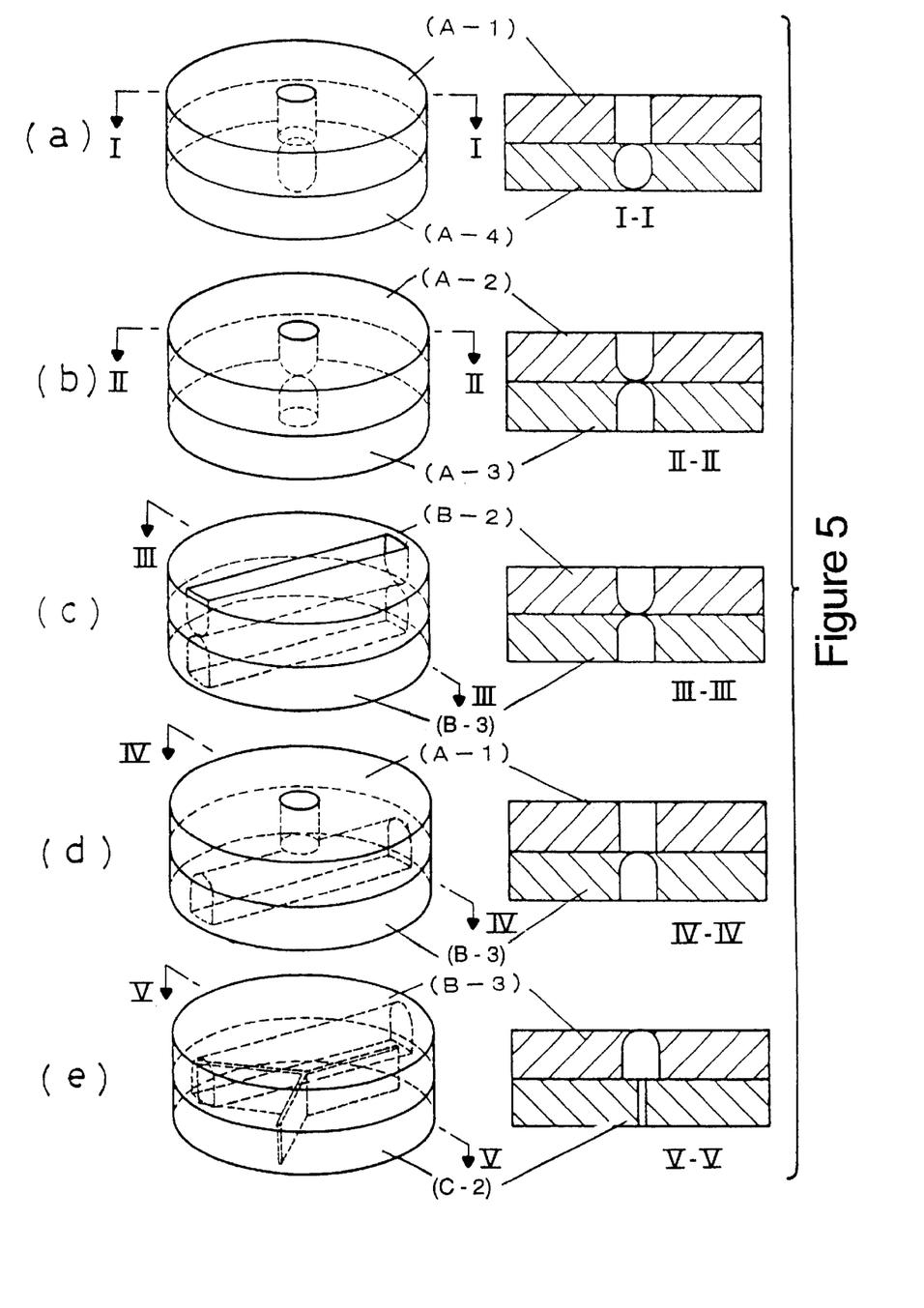
FIG. 5 is a drawing illustrating a 2-layer hemostatic valve.

FIGS. 2 and 3 are schematic views and sections thereof where a pattern of small penetration holes and a pattern of narrow slits adopted in each layer of the hemostatic valve of the invention are exaggeratedly shown, and FIG. 5 is a drawing illustrating a pattern of cuts, and the hemostatic valve 5 is composed of these patterns.

The small penetration hole A penetrates perpendicularly through the center, and pattern A-1 is a complete straight hole which is widely open at both front and back sides, and in patterns A-2 and A-3, the front or back side is made spherical in contact with the surface of the inner wall of the small penetration hole A and made thinner in the center having a pin hole closed with flap 7.

In pattern A-4, both sides are formed into a pin hole structure closed with flap 7 having the same form as described above.

Slit B is formed into pattern B-1 having a straight structure of constant width or patterns B-2 and B-3 having a cut structure where its section at the front or back side is shaped in an arc form and made thinner at the center closed with flap 8.

In pattern B-4, a round hole having the same thickness is formed in parallel to with the front and back faces such that the outer periphery is contacted with both the faces whereby both the faces are formed into a cut structure closed with flap 8.

Figure 4:
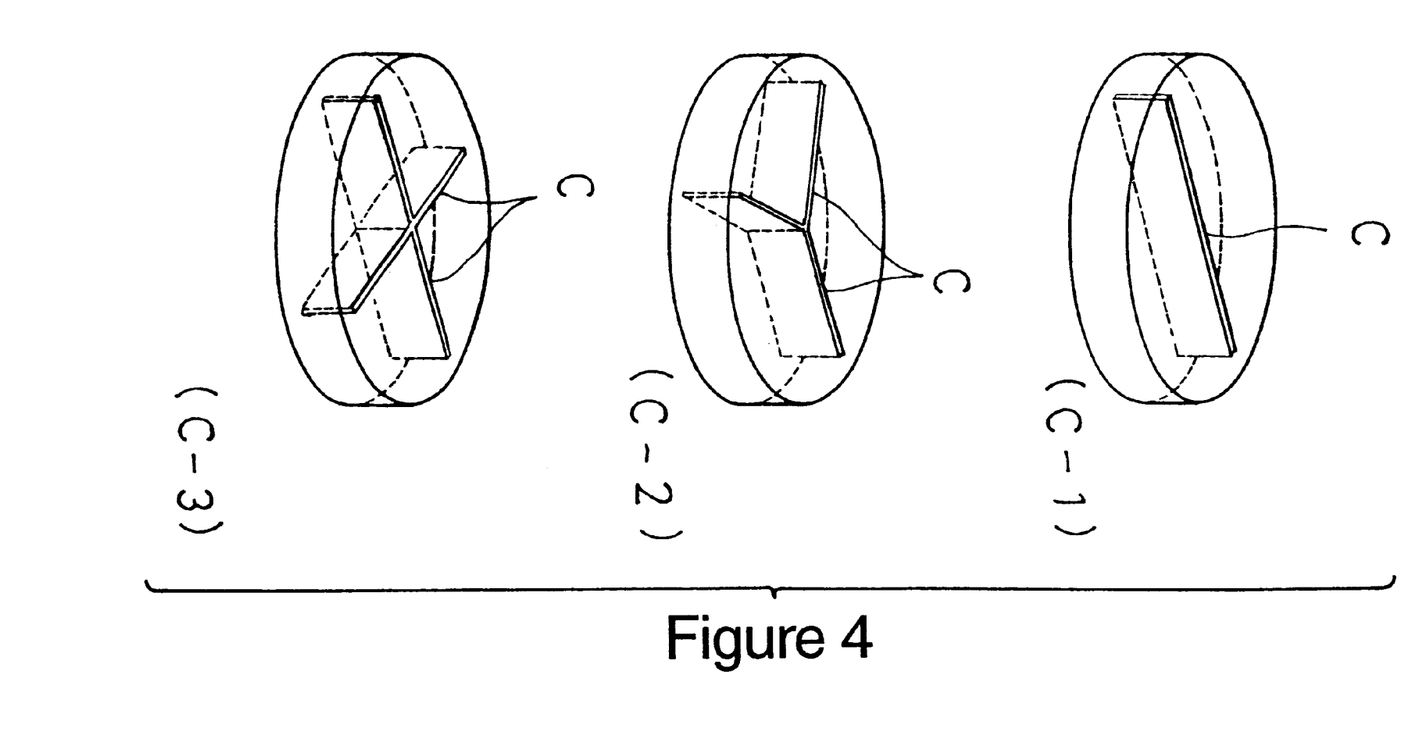
FIG. 4 is a drawing showing a pattern of cuts.

Further, referring to FIG. 4 cut C is a cut structure cut with a knife and is shaped into one letter such as in pattern C or into a Y or X shape having a crossing at the center, such as in patterns C-2 and C-3.

Figure 6:
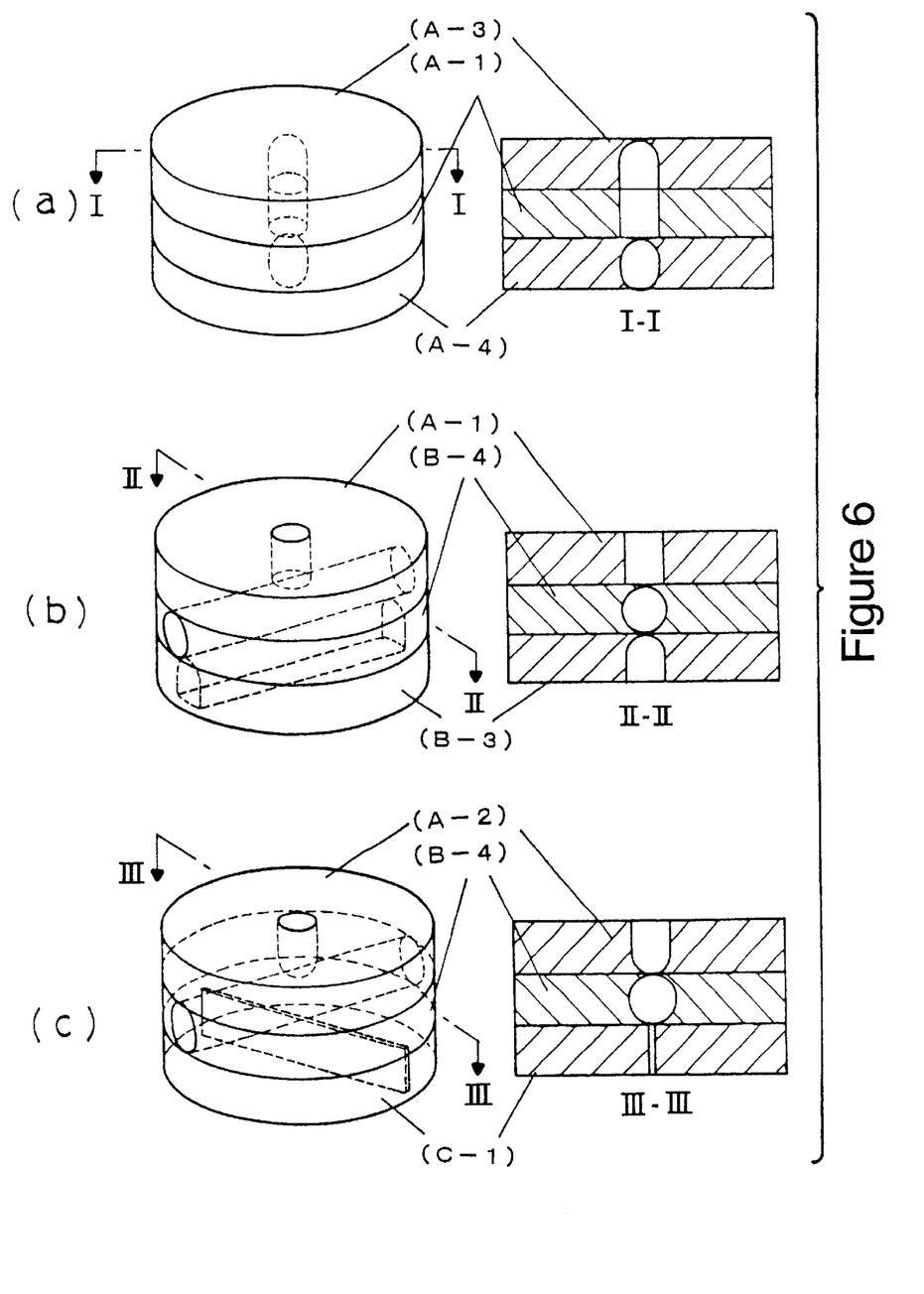
FIG. 6 is a drawing illustrating a 3-layer hemostatic valve.

Referring to FIG. 5 and FIG. 6 non-limiting examples of two-layer structures as combinations of these patterns include combinations of small penetration holes such as a combination of pattern A-1 and pattern A-4 (a in FIG. 5) and a combination of pattern A-2 and pattern A-3 (b in FIG. 5), combinations of overlaid slits where cuts overlap with each other, such as in a combination of patterns B-2 and B-3 (c in FIG. 5), a combination of a small penetration hole and a slit such as in a combination of patterns A-1 and B-3 (d in FIG. 5), a combination of a slit and a cut such as in a combination of patterns B-3 and C-2 (e in FIG. 5), and arbitrary 3-layer combinations of a small penetration hole, a slit and a cut, such as in a combination of patterns A-3, A-1 and A-4 (a in FIG. 6), a combination of patterns A-1, B-4 and B-3 (b in FIG. 6), and a combination of patterns A-2, B-4 and C-1 (c in FIG. 6), so there can be a wide variety of forms where a flap is located in the front and/or backface or in the boundary face.

However, a combination of cuts, through-holes or straight grooves among themselves is excluded.

The small penetration hole A and the narrow slit B are opened in an ordinary state in the absence of external force, and in this state, the width of the slit is 0.2 mm when the diameter of the valve is 7 mm.

The combination of different types or the same type of patterned layers gives a pin hole structure in which a flap is protruded from the surrounding to the center in the front and/or back face or in the boundary, or a cut structure in which flaps are projected from both sides.

Figure 7:
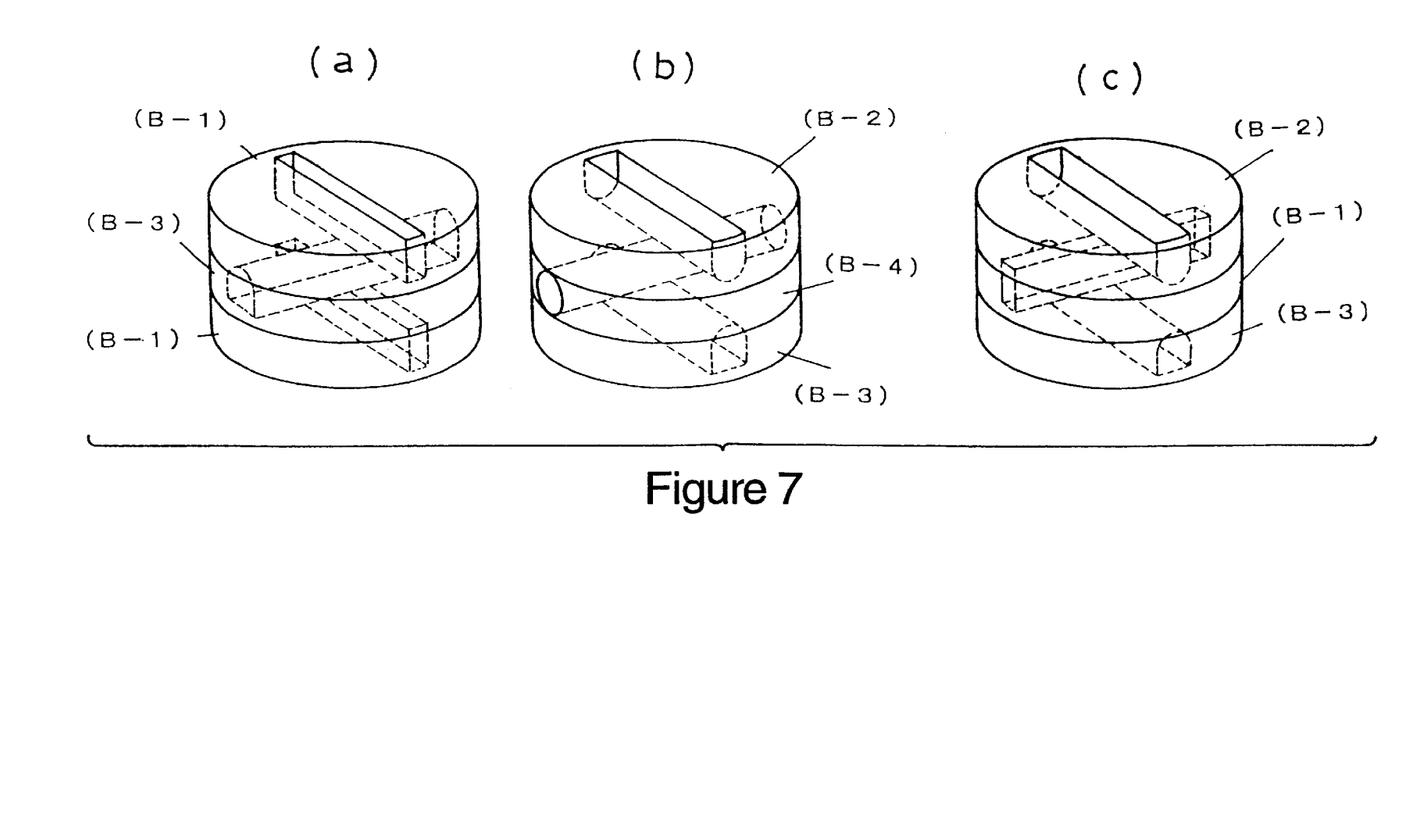
FIG. 7 is a drawing illustrating a combination of narrow slits exclusively.
Figure 8:
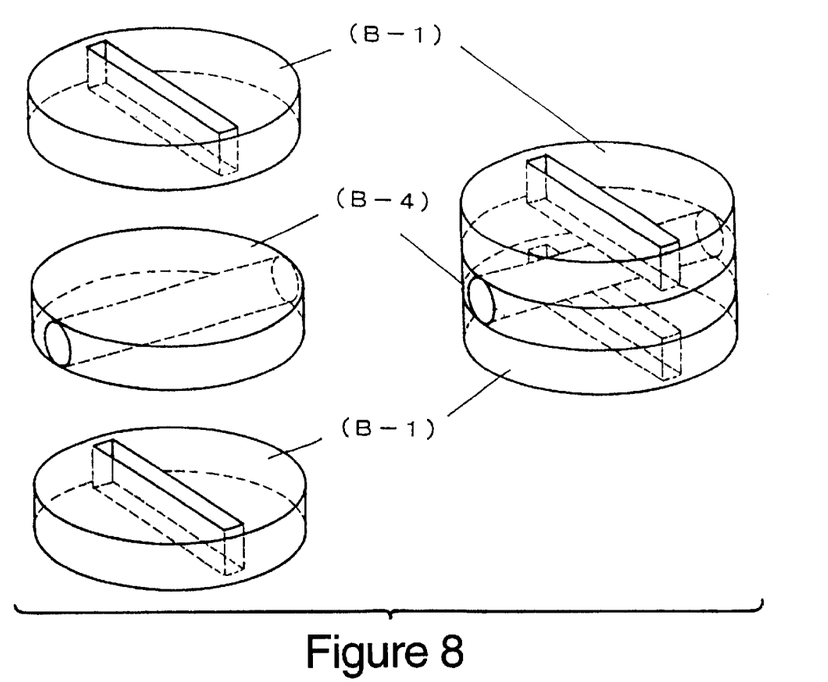
FIG. 8 is a drawing showing a preferable combination of narrow slits exclusively.

Referring to FIG. 7 and FIG. 8, even the combination of only narrow slits includes a combination of patterns B-1, B-3 and B-1 (a in FIG. 7), a combination of patterns B-2, B-4 and B-3 (b in FIG. 7) and a combination of patterns B-2, B-1 and B-3 (c in FIG. 7), but the combination of B-1, B-4 and B-1 as shown in FIG. 8 is simple and exhibits high hemostatic effects.

Figure 9:
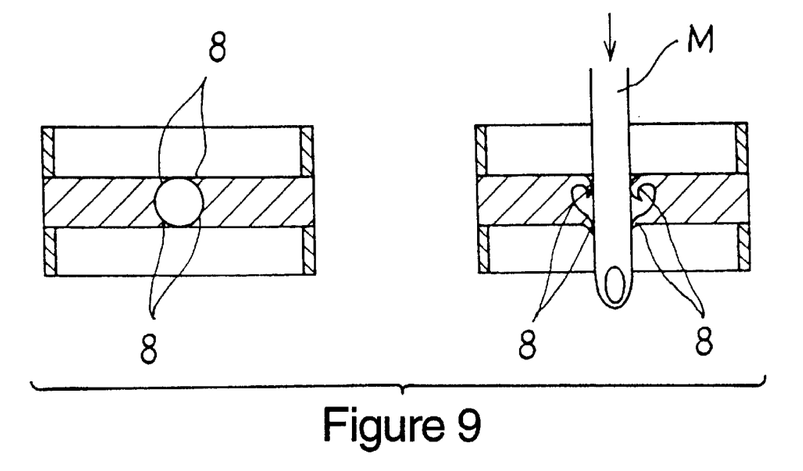
FIG. 9 is a drawing showing the state of being opened by insertion of a catheter.

In this combination, flap 8 can be easily opened by inserting catheter M, as shown in FIG. 9.

A layer having flaps 8 formed at both openings by providing a penetration hole having a circular section is arranged as the interlayer, thereby achieving a double hemostatic portion and a double hemostatic function.

The hemostatic vessel thus formed is attached to the valve accommodating portion in the catheter introducer whereby a high hemostatic effect can be achieved even without tightening the hemostatic valve by external force.

Further, the blood is prevented from being leaked from the surface slit through the outer periphery of the valve into the slit at the back.

Figure 10:
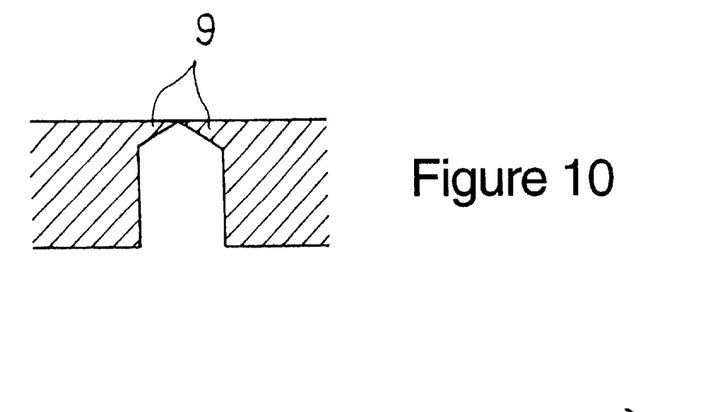
FIG. 10 is a drawing showing a modification to flap formation.

In the example illustrated above, a section of the small penetration hole is made circular, and the opening of said penetration hole is made to have a spherical face in contact with the boundary of a layer, or a section of the opening of the narrow slit is made to have a curved face in contact with the boundary of a layer thereby forming a flap, but the section of the opening can be made not only circular or curved but also polygonal to form flap 9 as shown in FIG. 10.

In any cases, the opening is closed in an ordinary form, and the hemostatic function can work in the absence of a tightening force, and because of the absence of a tightening force, the resistance of a catheter in passing through the hemostatic valve becomes less, thus making the valve suitable for use in a catheter introducer.

The hemostatic valve of the invention can be developed into a valve having 3 or more layers where the layers separately formed may be attached into one body or may be formed into one body from the start, and the main body 1 of the valve may be composed of any material such as latex rubber, thermoplastic resin, thermosetting resin and elastic materials in addition to silicon rubber.

The structure and shape of the catheter introducer is not limited to the example illustrated above, and its operativeness can further be improved by making a modification to the width of the slit.

Figure 11:
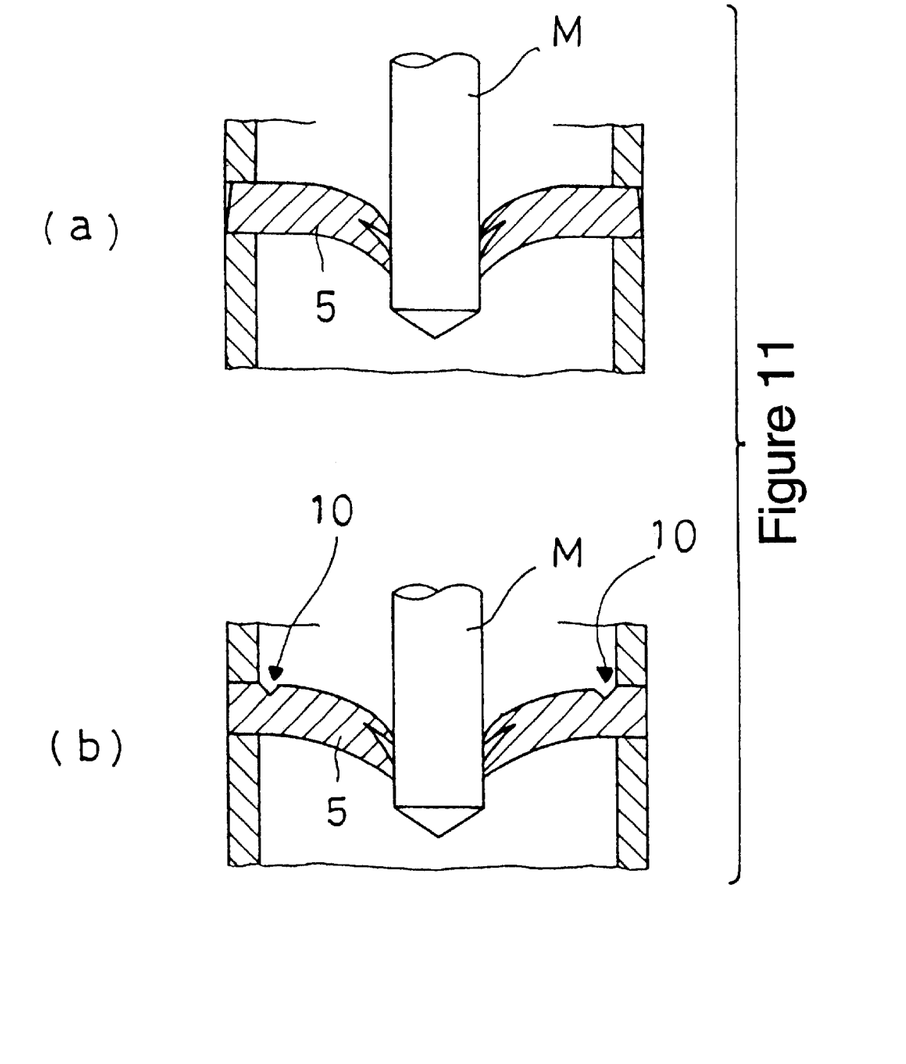
FIG. 11 is a drawing showing the hemostatic valve provided with a groove along the outer periphery on the face at the side for inserting a catheter.

Further, when a catheter is inserted into the small penetration hole or the narrow slit in the hemostatic valve, the edge of the slit is pushed together with the flap, thus pulling the outer periphery and worsening its adherence to the vessel accommodating portion, as shown in FIG. 11(*a*), but if a V-shaped groove 10 is formed along the edge on the face at the side for insertion of a catheter, the groove 10 is opened as shown in FIG. 9(*b*), and even if the central portion of the hemostatic valve 5 is pushed, the pushing effect does not extend to the outer periphery, so the adherence of the edge to the valve accommodating portion is maintained.

Even if a cut is provided in place of said groove, the same effect can be expected.

The effect of the invention is as follows:

The hemostatic valve 5 of the invention can be used to conduct the insertion and removal of a catheter M smoothly.

A section of the small penetration hole is made circular, and the opening of said penetration hole is made to have a spherical face in contact with the boundary of a layer, or a section of the small penetration hole is made polygonal and the opening of said penetration hole is made to have a polygonal pyramid-shaped face having a tip in contact with the boundary of a layer, or a section of the opening of the narrow slit is made with a curved face having a tip in contact with the boundary of a layer, or a section of the opening of the narrow slit is formed into a polygonal shape having a tip in contact with the boundary of a layer, whereby the flap can be reasonably formed.

Further, if a groove is formed along the edge on the face at the side for insertion of a catheter, M the deformation due to the operation of inserting and removing a catheter M does not extend to the outer periphery, and the adherence of the edge to the valve accommodating portion is maintained.

What is claimed is:

1. A hemostatic valve for a catheter introducer having a main body formed with plural layers, each of said plural layers having any one of a small penetrating hole, narrow slit, and a cut, each small penetrating hole passing through the center of a corresponding layer, each narrow slit passing across the center of a corresponding layer, each cut passing across the center of a corresponding layer, wherein said plural layers comprise at least one type of said layers with said small penetrating hole or said layers with said narrow slit, and each said small penetrating hole or said narrow slit having a spherical side to provide a closed flap at a site opening to a boundary between the corresponding layer and a layer adjacent thereto.

2. The hemostatic valve for a catheter introducer according to claim 1 wherein each section of each small penetration hole is circular.

3. A hemostatic valve for a catheter introducer according to claim 1 wherein a groove is provided around an outer edge on the side of said valve for inserting a catheter.

4. A hemostatic valve for a catheter introducer according to claim 2 wherein a groove is provided around an outer edge on the side of said valve for inserting a catheter.

5. A hemostatic valve for a catheter introducer have a main body formed with plural layers, each of said plural layers having any one of a small penetration hole, narrow slit, and a cut, each small penetration hole passing through the center of a corresponding layer, each narrow slit passing across the center of a corresponding layer, each cut passing across the center of a corresponding layer, wherein said plural layers comprise at least one type of said layers with a small penetration hole or said layers with a narrow slit, each said small penetration hole or said narrow slit having a closed flap provided at a site opening to a boundary between the corresponding layer and a layer adjacent thereto; and     each section of each small penetration hole is polygonal, the shape of an end of an opening of said penetration hole comprises a polygonal pyramid to contact with said boundary between layers to form said flap.

6. A hemostatic valve for a catheter introducer according to claim 5 wherein a groove is provided around an outer edge on the side of said valve for inserting a catheter.

7. A hemostatic valve for a catheter introducer having a main body formed with plural layers, each of said plural layers having any one of a small penetrating hole, narrow slit, and a cut, each small penetrating hole passing through the center of a corresponding layer, each narrow slit passing across the center of a corresponding layer, each cut passing across the center of a corresponding layer, wherein said plural layers comprise at least one type of said layers with said small penetrating hole or said layers with said narrow slit, each said small penetrating hole or said narrow slit having a closed flap provided at a site opening to a boundary between the corresponding layer and a layer adjacent thereto; and     a section of said opening of said narrow slit being curved to contact with said boundary of layers to form said flap.

8. A hemostatic valve for a catheter introducer according to claim 7 wherein a groove is provided around an outer edge on the side of said valve for inserting a catheter.

9. A hemostatic valve for a catheter introducer having a main body formed with plural layers, each of said plural layers having any one of a small penetrating hole, narrow slit, and a cut, each small penetrating hole passing through the center of a corresponding layer, each narrow slit passing across the center of a corresponding layer, each cut passing across the center of a corresponding layer, wherein said plural layers comprise at least one type of said layers with said small penetrating hole or said layers with said narrow slit, each said small penetrating hole or said narrow slit having a closed flap provided at a site opening to a boundary between the corresponding layer and a layer adjacent thereto; and     a section of an end of an opening of said narrow slit comprises a polygonal face to contact with said boundary between layers to form said flap.

10. A hemostatic valve for a catheter introducer according to claim 9 wherein a groove is provided around an outer edge on the side of said valve for inserting a catheter.

* * * * *